United States Patent [19]

Bozzo

[11] Patent Number: 5,085,664

[45] Date of Patent: Feb. 4, 1992

[54] DISOBSTRUCTOR DILATOR DEVICE FOR URINARY PATHOLOGY

[76] Inventor: Luigi Bozzo, 7, via Trieste, Genova, Italy

[21] Appl. No.: 379,218

[22] Filed: Jul. 13, 1989

[30] Foreign Application Priority Data

Jul. 22, 1988 [IT] Italy ............................ 12527 A/88

[51] Int. Cl.⁵ .................................................. A61F 2/02
[52] U.S. Cl. .................................... 606/191; 621/1
[58] Field of Search ................................ 623/1, 12; 604/104–109; 606/153, 191, 194; 600/29, 30

[56] References Cited

U.S. PATENT DOCUMENTS

| | | | |
|---|---|---|---|
| 3,397,699 | 8/1968 | Kohl | 604/105 |
| 3,592,197 | 7/1971 | Cohen | 604/106 |
| 4,776,337 | 10/1988 | Palmaz | 623/1 |
| 4,795,458 | 1/1989 | Regan | 623/1 |

FOREIGN PATENT DOCUMENTS

| | | | |
|---|---|---|---|
| 2827908C2 | 1/1980 | Fed. Rep. of Germany. | |
| 2827908 | 6/1982 | Fed. Rep. of Germany. | |
| 0040812 | 12/1908 | France | 604/106 |
| 0339087 | 10/1936 | Italy | 604/105 |

*Primary Examiner*—C. Fred Rosenbaum
*Assistant Examiner*—William W. Lewis
*Attorney, Agent, or Firm*—Larson and Taylor

[57] ABSTRACT

The disobstructor dilator device (1) is employed in the urinary obstructive pathology of the cervico-urethral portion of the male, in order to ensure the openness of the urethral channel between the vesical neck and the striated sphincter of the urethra. The device (1) consists of a tubular body (101) open at its ends, in which the lower end presents a section which is greater than the upper end. At the upper end there are provided anchoring elements (2) having the shape of hooks, which are intended to cooperate with the vesical neck (12).

6 Claims, 4 Drawing Sheets

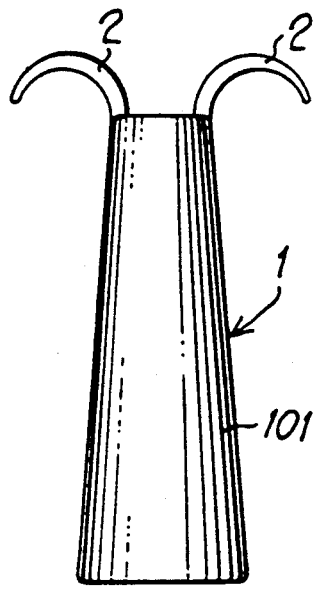
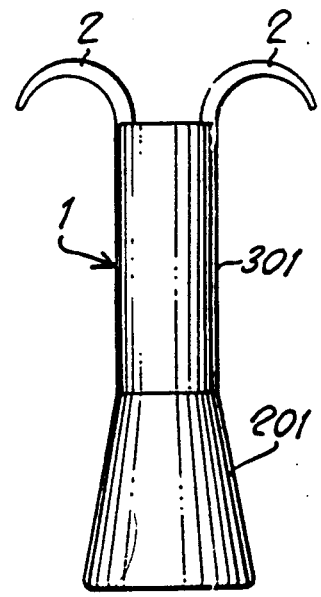
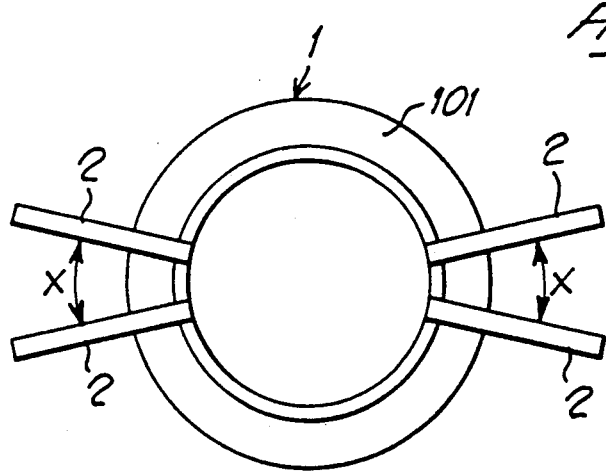
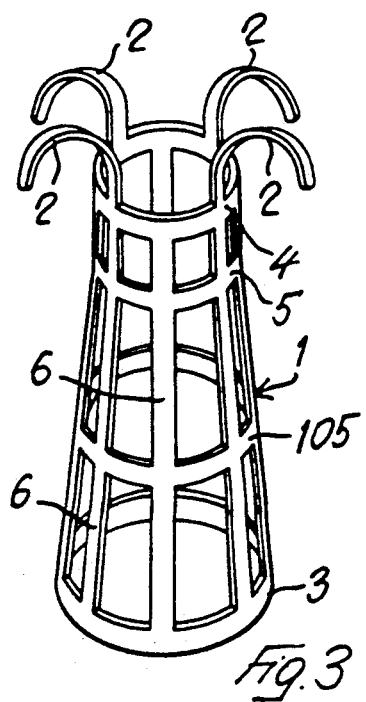
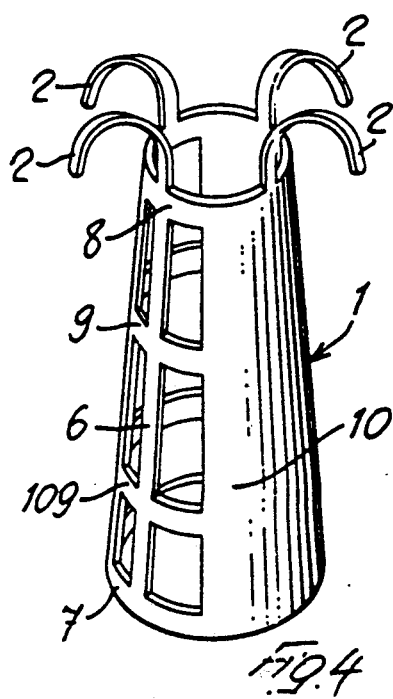

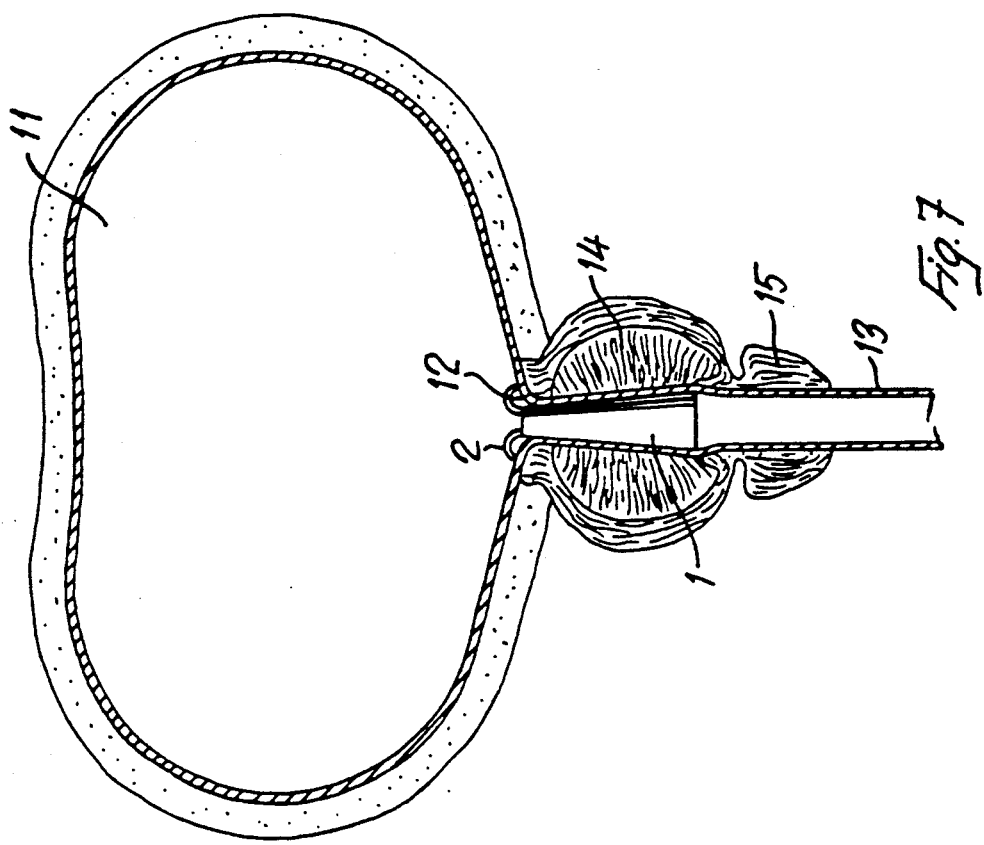
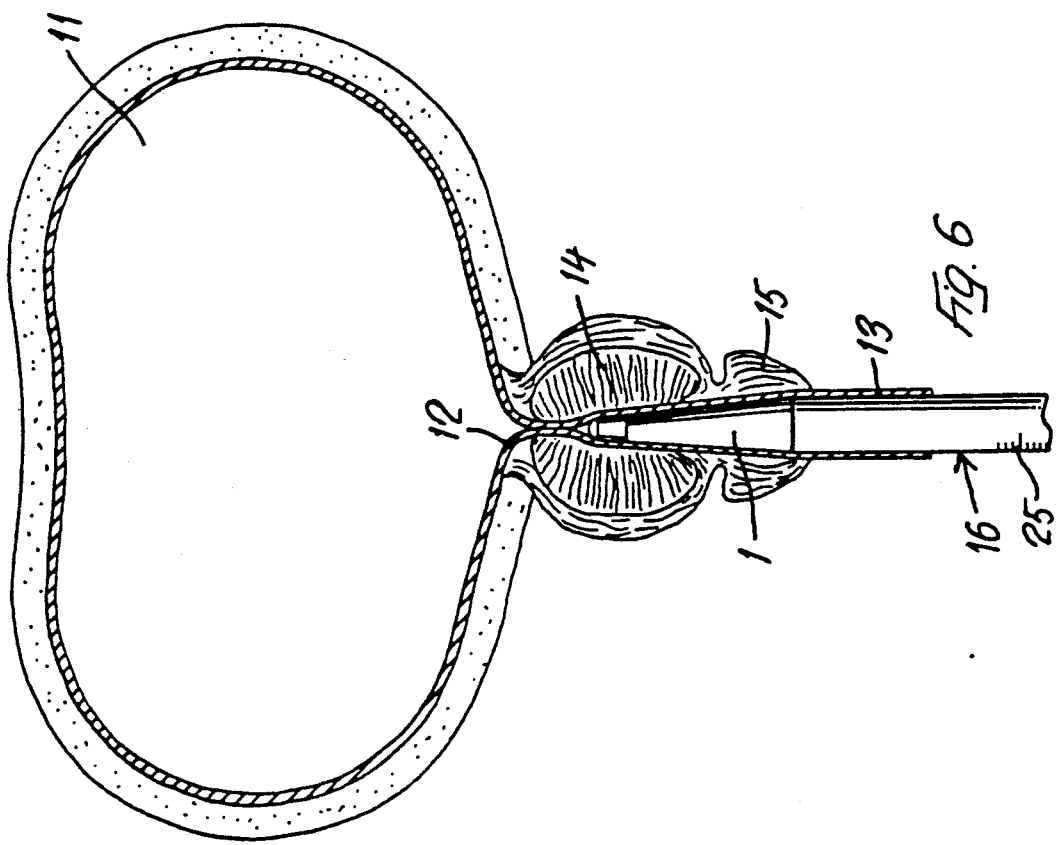

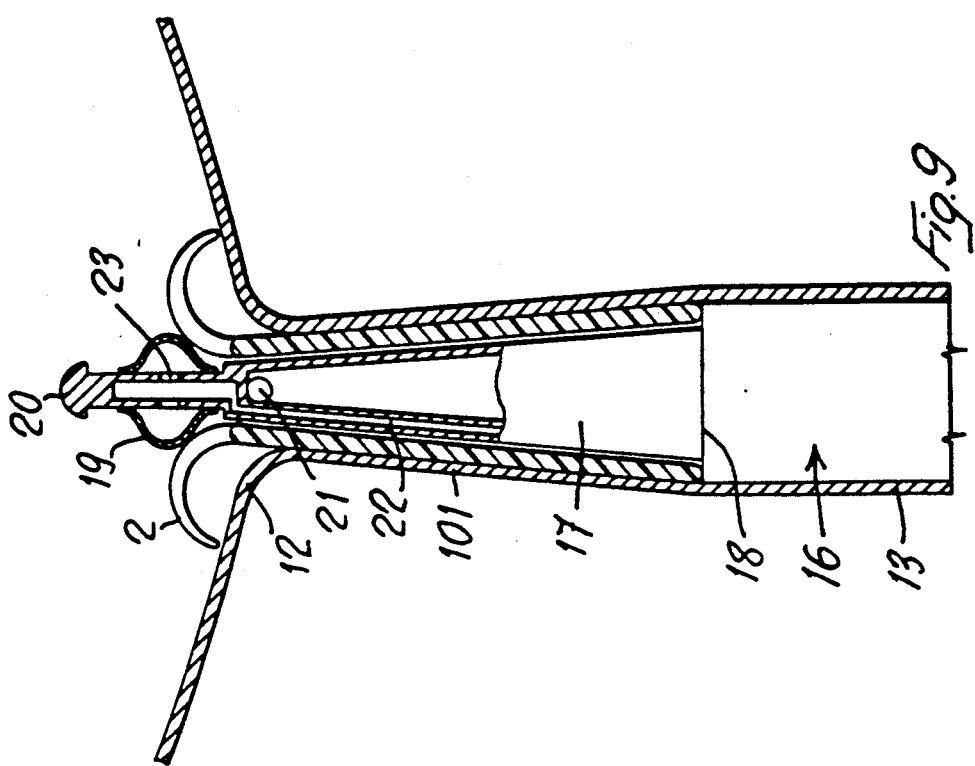
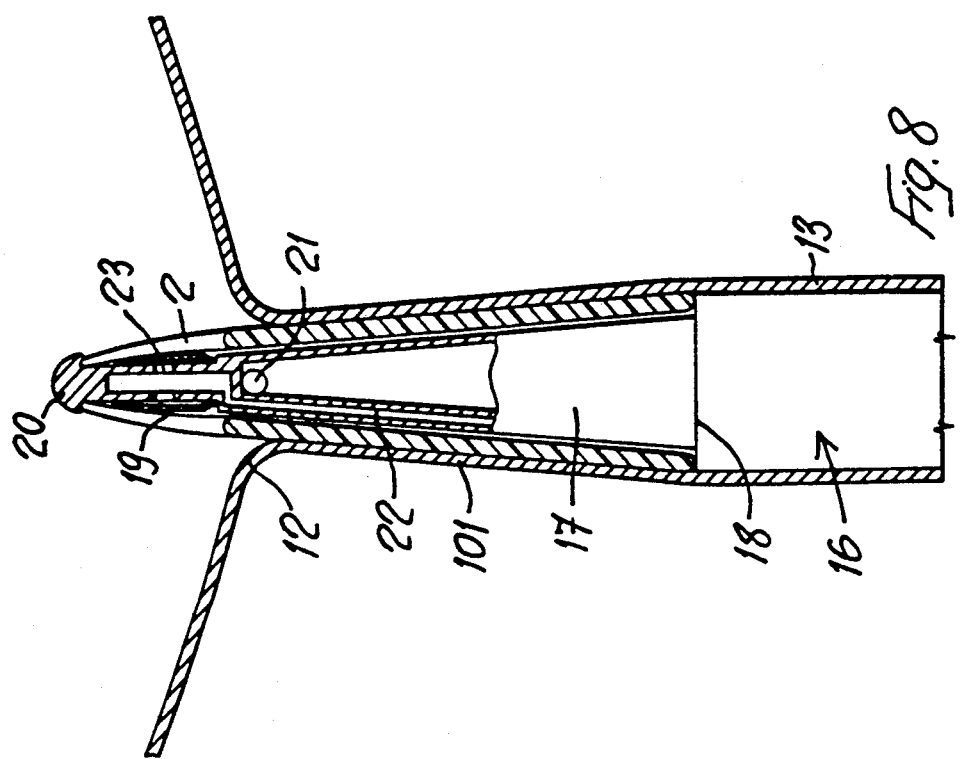

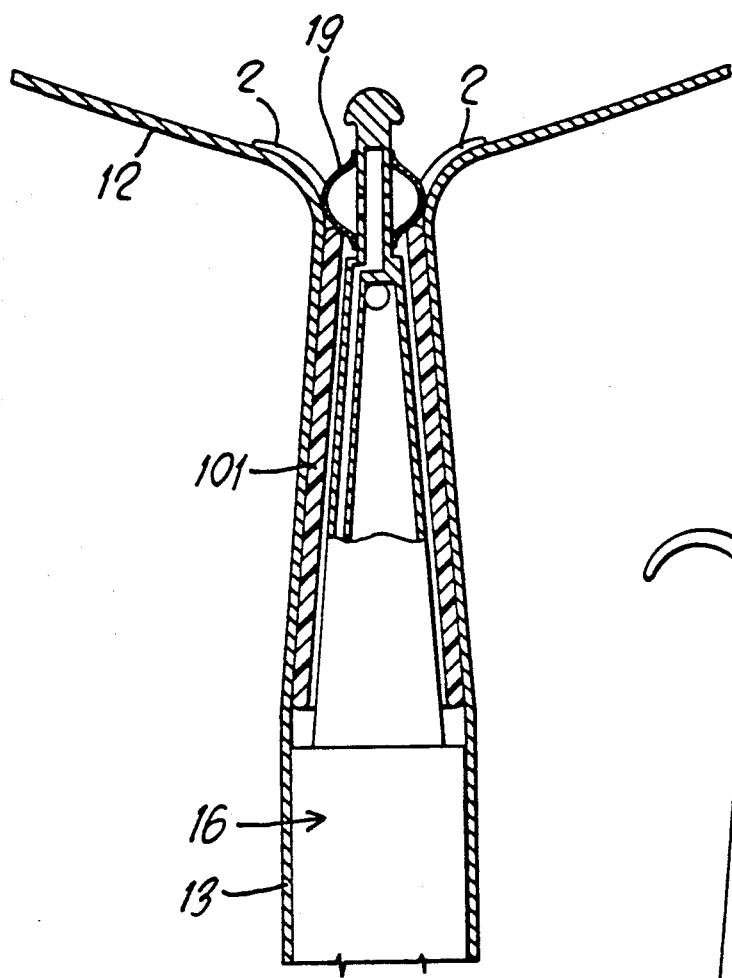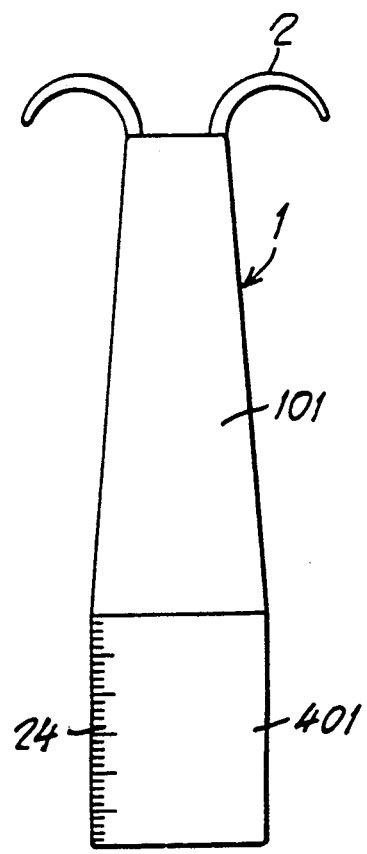
Fig. 10
Fig. 11

DISOBSTRUCTOR DILATOR DEVICE FOR URINARY PATHOLOGY

The present invention relates to a disobstructor dilator device which is employed in the urinary obstructive pathology of the male, in order to ensure the openness of the urethral channel between the vesical neck and the striated sphincter of urethra.

In the urinary pathology of the male there arises with a certain frequency the case in which (for example due to a swelling of the prostate gland) there takes place a total or partial obstruction of the urethral channel in the zone comprised between the vesical neck and the striated sphincter of the urethra. In such cases, the use of a catheter certainly re-establishes the openness of the urethral channel, but it does not permit the spontaneous urination, since the catheter occupies also the zone of the striated sphincter muscle of the urethra.

The purpose of the device according to the invention is to restore the voluntary mechanism of the urination, in those cases in which this latter is prevented by an obstruction of the cervico-urethral zone, between the vesical neck and the striated sphincter of the urethra.

The use of the device according to the invention can be therefore:

definitive, in those cases in which it is not possible to perform a therapy which permits the disobstruction of the urethral channel;

temporary, in other cases in which it is necessary to wait for the radical correction of the obstructive symptom;

diagnostic, in all cases in which it is desired to evaluate the influence of the cervico-urethral zone in the retention of urine.

German patent DE-C2-2 827 908 (FABIAN) discloses a device which is inserted through the urethral channel up to the prostate. The device consists of a cylindrical tube made of helically wound wire, in which the lower end of the tube continues with a short length of straight wire terminating with an anchoring ring. The device is positioned with the tube in the zone of the prostate, while the anchoring ring comes to be positioned below the sphincter muscle of the urethra. The straight wire connecting the tube to the anchoring ring comes therefore to be positioned at the zone of the sphincter muscle, so as to interfere minimally with the function of said muscle. The above disclosed device will therefore act as a disobstructor dilator device wich permits spontaneous urination.

According to the present invention, the disobstructor dilator device substantially consists of a tubular body open at its ends, made of any suitable material, in which the lower end presents a section which is greater than the section of the upper end. At the upper end there are provided anchoring hooks intended to cooperate with the vesical neck. The device is positioned in the cervico-urethral zone of the urethral channel, between the urethral neck and the striated sphincter muscle, sufficiently above this latter, so as to permit the function of the muscle itself in a totally free manner. The shape, presenting a lower base which is greater, prevents the sliding of the device into the bladder, while the downward expulsion towards the exterior is prevented by the presence of the elastic hooks which anchor themselves onto the vesical neck.

The invention relates further to an inserter-extractor instrument for inserting in place the disobstructor device and for its removal.

Further characteristic features and advantages of the disobstructor device and of the inserter-extractor instrument according to the invention will appear evident from the following description of some preferred embodiments, made, by way of non-limiting example, with reference to the figures of the attached drawings, in which:

FIG. 1 is a side elevation view of a first embodiment of the device according to the invention;

FIG. 2 is a side elevation view of a second embodiment of the device according to the invention;

FIG. 3 is a perspective view of a third embodiment of the device, presenting a reticulate structure;

FIG. 4 is a perspective view of a fourth embodiment of the device, presenting a reticulate-and-continuous compound structure;

FIG. 5 is a plan view from the top of the device according to FIG. 1, in an enlarged scale;

FIG. 6 shows diagrammatically the device during its application;

FIG. 7 is a view analogous to that of FIG. 6, showing the device as applied;

FIGS. 8, 9 and 10 show diagrammatically the disobstructor device together with the inserter-extractor instrument during the steps of insertion, application and extraction of the device;

FIG. 11 is a side elevation view of a further embodiment of the device according to the invention.

In the description which follows, the terms "lower" and "upper", "front" and "back", referred to the device object of the invention or to parts thereof are to be considered with reference to the position in place of the device itself, applied to the patient in upright position.

With particular reference to FIG. 1, the disobstructor dilator device 1 consists of a tubular body 101 open at its ends, having substantially the shape of a frustum of a cone, and provided at its upper end (having a smaller diameter) with a plurality of anchoring elements 2, each shaped like a hook with the point directed towards the exterior and the greater base. Both the tubular body 101 and the hooks 2 are made of any suitable material known to a person skilled in the art, for instance rubber or silicone resin. The hooks 2 are elastic and therefore may be bent towards the interior, so as to be substantially aligned with the generatrices of the body having the shape of the frustum of a cone, for the purposes which will be seen after, while their normal position is the active one, shown in FIGS. from 1 to 5.

The hooks 2 are at least two and preferably they are four, as shown in FIG. 5, arranged by diametrally opposed pairs, the angular distance between the hooks of each pair being between 45° and 15°, and preferably 25°.

In FIG. 2 there is shown another embodiment of the disobstructor device 1, in which same is shaped like a funnel so as to present a lower portion 201 shaped like the frustum of a cone and an upper portion 301 which is substantially cylindrical, the hooks 2 being arranged at the upper open end of the cylindrical portion 301.

FIG. 3 shows a disobstructor device 1 having a reticulate structure. More particularly, said structure consists of a series of rings 3, 4, 5, 105 parallel to one another, connected by means of longitudinal strips 6. As it can be appreciated, the device comprises a lower end ring 3, of greater diameter, and an upper end ring 4, of smaller diameter, as well as intermediate rings 5, 105. In order to confer to the body the required stiffness, the longitudinal connecting strips 6 will be at least three. In the shown embodiment, the anchoring hooks 2 are arranged as a continuation of the upper end of some of the connecting strips 6. The device according to FIG. 3 presents a substantially funnel-shaped reticulate body, in which the intermediate ring 5 constitutes the union between the lower element shaped like the frustum of a cone (3, 105, 5) and the upper cylindrical element (5, 4).

In FIG. 4 there is shown a further embodiment of the disobstructor device 1, in which the tubular body shaped like the frustum of a cone consists partially of a continuous wall, and partially of a reticulate wall, said two walls being arranged side by side longitudinally. In transverse section, the continuous wall 10 and the reticulate wall extend each along about 180°. The reticulate wall consists of a lower semiring 7, of an upper end semiring 8 and of the intermediate semirings 9, 109.

With particular reference to FIGS. 6 and 7, there is shown the scope of application and the mode of operation of the disobstructor dilator device according to the invention. Diagrammatically, in said Figures, reference numeral 11 indicates the urinary bladder of the male, viewed frontally, which terminates at the bottom into the vesical neck 12 which continues into the urethral channel 13. For the purposes of merely illustrating the application and the function of the device object of the invention, there are further diagrammatically shown the prostate gland 14 and the striated sphincter muscle 15 of the urethra.

As it can be appreciated from FIG. 6, as the consequence of any whatsoever pathological condition, the cervico-urethral zone of the urethra 13 (located between the vesical neck 12 and the sphincter muscle 15) can be totally or partially obstructed, for example due to a swelling of the prostate gland 14. Under such conditions, the application of the disobstructor device according to the present invention overcomes the obstacle deriving from said pathological condition, by permitting the spontaneous urination. With the aid of a suitable inserter instrument 16, the disobstructor device 1 is inserted (see FIG. 6) through the urethral channel 13 up to the cervico-urethral zone. During said phase of insertion, the anchoring elements or hooks 2 are bent in such a manner as to be aligned at least approximately according to the generatrices of the tubular body of the device itself, so that they do not create an obstacle to the insertion and passing of the device through the urethra.

After the positioning of the device 1 in the cervico-urethral zone, with its upper end (presenting a smaller diameter) approximately at the level or slightly above the vesical neck 12, and the lower end (presenting a larger diameter) above the striated sphincter 15, the hooks 2 are set free (through suitable means which will be described after). The said hooks open themselves elastically and come to bear against the vesical neck 12. In such a manner, the device 1 is blocked in position in a stable and safe manner, since it is prevented from sliding downward by the hooks 2, while it cannot further slide upwardly (into the interior of the urinary bladder 11) because of its shape.

In such a manner, there is ensured the openness of the urethral channel in the zone concerned by the device, while the possibility of spontaneous urination is also ensured, since the striated sphincter muscle 15 is not affected by the said device.

With particular reference to FIGS. 8 to 10, there is shown, merely by way of example, an inserter-extractor instrument for the device according to the present invention, respectively during the step of insertion (FIG. 8), of application (FIG. 9) and of extraction (FIG. 10) of the device itself.

As it can be seen from said Figures, the inserter-extractor instrument 16 consists of a catheter of the balloon type, which has its distal end suitably modified. More precisely, said end presents a seat 17 apt to house at its exterior the tubular body 101 of the disobstructor device. In the present case, merely by way of example, the disobstructor device is of the type shown in FIG. 1 and therefore is shaped like the frustum of a cone. Obviously, in case of configurations of the device which are different from the frustum of a cone, also the seat 17 of the inserter device 16 will be correspondingly modified. The seat 17 terminates with an annular step 18 which ensures the staying in place of the disobstructor device during the insertion maneuver. At the top of the catheter 16, above the balloon 19, there is provided a retaining element 20 which is shaped like a mushroom cap.

The disobstructor device 101-2 is mounted onto the instrument 16, for its application in place, by bending the hooks 2 into alignment with the generatrices of the tubular body 101, in such a manner that the free ends of the said hooks can be inserted below the lower circular crown of the mushroom cap 20, so that they are temporarily blocked in said position. Obviously, the balloon 19 is kept deflated (FIG. 8).

At this stage, the inserter catheter instrument 16 is inserted through the urethra, until it reaches the vesical neck 12. The correct positioning of the inserted instrument will be indicated by the outflow of urine through the hole 21, in a known manner. At this stage, as shown in FIG. 9, through the duct system 22-23, there is promoted the inflation of the balloon, which sets free the ends of the hooks 2 from the mushroom cap 20, and causes the consequent anchorage of the said hooks onto the vesical neck. Subsequently, after having deflated the balloon 19, the inserter instrument 16 can be freely removed, thus leaving the disobstructor device correctly positioned.

When it is desired to extract the disobstructor device 101-2, the process is reversed, as shown in FIG. 10. The catheter extractor instrument 16 is inserted through the urethra 13, with the balloon 19 in its deflated condition. As soon as the balloon 19 has passed over the upper end of the tubular body 101, it is inflated of such an amount that its maximum outer diameter substantiantially corresponds to the outer diameter of the upper end of tubular body 101. At this point, by pulling back the instrument 16, the balloon 19 will engage, during its extraction movement, the said upper end of the tubular body 101, and therefore will entrain it in its descent. The anchoring hooks 2 will practically oppose no resistance to said movement, in consideration of their elasticity. The positioning of the extractor catheter can be facilitated by the presence along same of reference marks 25 which permit the exact determination of the depth of insertion of the said catheter.

In relation to possible difficulties during the extraction step of the disobstructor device, deriving from the conformation of the urethral channel, it may be convenient to use the disobstructor device according to FIG. 4 (see above): in fact, the position in place of same with its continuous wall arranged at the back, will avoid any possible interference between the extractor instrument 16 and the intermediate rings of the disobstructor device, when the extractor instrument is inserted and caused to advance inside the urethral channel.

Obviously, the device according to the invention can be constructed of different sizes, both in length and in section, depending upon the anatomical requirements of the patient, said sizes being suitably indicated on the device itself.

With reference to FIG. 11, same shows a further embodiment of the disobstructor device according to the invention, which is particularly adapted whenever it is desired to modify proportionately, depending upon the anatomical features of the patient, the length of the device itself. The device 1 consists of a tubular body 101, analogous to the one shown in FIG. 1 which, at its lower end (having a greater diameter) continues with a cylindrical portion 401, which can be suitably provided along its longitudinal direction with graduated reference marks 24 which precisely divide the length of the said cylindrical portion 401. It appears evident that, by cutting according to a definite measurement a suitable length of said cylindrical portion, it is possible to vary the total length of the device 1, without any modification of same, as far as its operation is concerned. Although in FIG. 11 the tubular body 101 has been shown as having the shape of a frustum of cone (analogous to the one shown in FIG. 1), it is evident that same can have any other shape and that the shape which has been illustrated has been given by way of example only.

Obiously, the number of the anchoring elements or hooks 2 can broadly vary: the preferential arrangement which has been indicated with reference to FIG. 5 (see above) can be considered as optimal, in consideration of the particular form of the vesical neck, by inserting the disobstructor device in such a manner that each pair of hooks engages respective opposed zones located laterally with respect to the urethral channel.

As usual, the material of which the disobstructor device is made can incorporate suitable dots which are radiologically opaque, in order to locate and follow the position of the device by means of radiography.

I claim:

1. A dilator device employed in the urinary tract of male to ensure the openness of the urethral channel in the cervicourethral zone between the vesical neck and the striated sphincter of the urethra, comprising a tubular body open at its ends, said ends being designated as the upper end and the lower end with reference to the position of the device in place applied to the patient in upright position, said tubular body having a length which is smaller than the distance between the vesical neck and the striated sphincter, in which the lower end has a greater cross section than that of the upper end, and anchoring means intended to cooperate with the vesical neck, being provided at the upper end of said tubular body.

2. A dialator device according to claim 1, wherein the tubular body is shaped substantially like the frustum of a cone.

3. A dialator device according to claim 1, wherein the anchoring elements consist of elastic hooks arranged along the circumference of the upper end of the tubular body.

4. A dialator device according to claim 3, wherein there are at least two hooks.

5. A dialator device according to claim 4, wherein there are four hooks arranged by diametrally opposed pairs, the angular distance between the hooks of each pair being between 45° and 15°.

6. A dialator device according to claim 5, wherein the angular distance between the hooks of each pair is of 25°.

* * * * *